United States Patent [19]
Cauwet et al.

[11] Patent Number: 5,935,587
[45] Date of Patent: *Aug. 10, 1999

[54] COSMETIC COMPOSITION CONTAINING AT LEAST ONE NON-IONIC SURFACTANT OF THE ALKYLPOLYGLYCOSIDE AND/OR POLYGLYCEROL TYPE, AND AT LEAST ONE POLYDIMETHYLSILOXANE/ POLYOXYALKYLENE BLOCK

[75] Inventors: Daniele Cauwet, Paris; Claude Dubief, Le Chesnay, both of France

[73] Assignee: L'Oreal, France

[*] Notice: This patent issued on a continued prosecution application filed under 37 CFR 1.53(d), and is subject to the twenty year patent term provisions of 35 U.S.C. 154(a)(2).

[21] Appl. No.: 08/689,273

[22] Filed: Aug. 6, 1996

Related U.S. Application Data

[63] Continuation of application No. 08/304,833, Sep. 13, 1994, abandoned.

[30] Foreign Application Priority Data

Sep. 14, 1993 [FR] France .................................. 93 10939

[51] Int. Cl.⁶ ............................. A61K 7/00; A61K 7/075; A61K 7/08; A61K 7/48
[52] U.S. Cl. ..................... 424/401; 424/70.1; 424/70.12; 424/70.31; 510/122
[58] Field of Search ................................ 429/70.1, 70.12, 429/70.31, 401, 78.03; 514/844, 846; 510/122

[56] References Cited

U.S. PATENT DOCUMENTS

| | | |
|---|---|---|
| 3,821,372 | 6/1974 | Vanlerberghe et al. .............. 424/70.31 |
| 3,928,558 | 12/1975 | Cheesman . |
| 4,307,079 | 12/1981 | Zorayan et al. ...................... 424/70.31 |
| 4,425,364 | 1/1984 | Vanlerberghe et al. ................... 424/64 |
| 4,515,775 | 5/1985 | Vanterberghe et al. ............. 424/70.31 |
| 4,656,030 | 4/1987 | Sebag . |
| 4,677,232 | 6/1987 | Sebag et al. ............................... 424/63 |
| 5,057,311 | 10/1991 | Kamegai et al. .................... 424/70.31 |
| 5,063,051 | 11/1991 | Grollier . |
| 5,180,584 | 1/1993 | Sebag et al. ............................. 424/401 |
| 5,194,260 | 3/1993 | Grollier et al. ......................... 424/401 |
| 5,324,507 | 6/1994 | Dubief . |
| 5,439,674 | 8/1995 | Noda et al. .......................... 424/70.12 |
| 5,536,493 | 7/1996 | Dubief ................................. 424/70.12 |
| 5,660,819 | 8/1997 | Tsubaki et al. ......................... 424/70.1 |

FOREIGN PATENT DOCUMENTS

| | | |
|---|---|---|
| 0398177 | 11/1990 | European Pat. Off. . |
| 0440542 | 8/1991 | European Pat. Off. . |
| 0492657 | 7/1992 | European Pat. Off. . |
| 0535367 | 4/1993 | European Pat. Off. . |
| 2242129 | 9/1991 | United Kingdom . |
| 9208439 | 5/1992 | WIPO . |

*Primary Examiner*—Robert H. Harrison
*Attorney, Agent, or Firm*—Cushman Darby & Cushman IP Group of Pillsbury Madison & Sutro LLP

[57] ABSTRACT

The invention relates to a cosmetic composition containing, in a cosmetically acceptable aqueous medium, at least one non-ionic surfactant of the alkylpolyglycoside family and/or a polyglycerol non-ionic surfactant, and at least one sequenced polydimethylsiloxane/polyoxyalkylene copolymer, as well as a process of cosmetic treatment consisting in applying a cosmetically effective quantity of this composition to keratinic materials.

24 Claims, No Drawings

COSMETIC COMPOSITION CONTAINING AT LEAST ONE NON-IONIC SURFACTANT OF THE ALKYLPOLYGLYCOSIDE AND/OR POLYGLYCEROL TYPE, AND AT LEAST ONE POLYDIMETHYLSILOXANE/POLYOXYALKYLENE BLOCK

This is a continuation of application Ser. No. 08/304,833, filed Sep. 13, 1994, now abandoned.

The invention concerns cosmetic compositions containing at least one non-ionic surfactant of the alkylpolyglycoside and/or polyglycerol type, and at least one polydimethylsiloxane/polyoxyalkylene block copolymer.

Polydimethylsiloxane/polyoxyalkylene block copolymers are known as conditioners in cosmetic compositions for the treatment of the skin or hair. They are described in Patent Application No. EP-049.26.57.

The surfactants of the alkylpolyglycoside or polyglycerol family have already been recommended in washing compositions for the hair or skin. They are mild detergents, well tolerated and bio-degradable.

The hair, attacked by atmospheric agents such as light or chemical treatment, and washed with conventional washing bases, is difficult to comb, and this drawback is even further accentuated in the case of fine hair.

Shampoo compositions which contain only non-ionic surfactants such as those listed above do not lead to good cosmetic properties, and, especially, the combing of wet hair is difficult and the hair in the dry state is rough.

The Applicant has surprisingly discovered that the combination, in washing and/or treating compositions for keratinic materials, of polydimethylsiloxane/polyoxyalkylene block copolymers, with particular non-ionic surfactants of the alkylpolyglycoside type and/or the polyglycerol type, imparts to these compositions considerably improved properties of combing wet hair, and of hair smoothing and styling.

In addition, the Applicant has found that such a combination imparts greater softness to the dry hair.

Furthermore, the compositions containing this combination offer greater ease of hair styling.

The present invention therefore has for object cosmetic compositions containing at least one non-ionic surfactant of the alkylpolyglycoside and/or polyglycerol type, and at least one polydimethylsiloxane/polyoxyalkylene block copolymer.

Another object of the invention is the use of these compositions for the treatment and/or washing of keratinic materials such as the skin or hair.

Another object of the invention concerns a process of cosmetic treatment of the hair and/or of the skin using these compositions.

The above and other objects and advantages of the invention will be apparent from the following description taken in conjunction with the accompanying examples.

The cosmetic compositions of the invention contain, in a cosmetically acceptable aqueous medium, at least one non-ionic surfactant of the alkylpolyglycoside and/or polyglycerol type, and at least one polydimethylsiloxane/polyoxyalkylene block copolymer.

The sequenced polydimethylsiloxane/polyoxyalkylene copolymers conforming to the present invention are preferably selected from among those answering to the formula:

$$([Y(R_2SiO)_aR_2SiYO][(C_nH_{2n}O)_b])_c \qquad (I)$$

where:

R is a monovalent hydrocarbon radical containing practically no unsaturated aliphatic groups, n is 2, 3 or 4, a is an integer not less than 5, b is an integer not less than 4, c is a number not less than 4, Y is a divalent organic group bound to an adjacent silicon atom by an Si/C bond and to a polyoxyalkylene block by an oxygen atom.

Copolymers with the formula (I) have an average molecular weight preferably of not less than 3000. The molecular weight of each siloxane block is between about 300 and 10,000. The molecular weight of each polyoxyalkylene block is between about 300 and 10,000. The proportion of siloxane blocks is between about 10 and 95% by weight of the total weight of the sequenced copolymer.

The R radicals are selected in particular from among the alkyl radicals such as methyl, ethyl, propyl, isopropyl, butyl, pentyl, hexyl, octyl, decyl, dodecyl, octadecyl and eicosyl, the aryl radicals, such as phenyl and naphthyl, the aralkyl radicals such as benzyl and phenylethyl, and the tolyl, xylyl or cyclohexyl radicals. They can be identical or different.

Among the organic divalent groups Y are the groups having the following structure:

$$-R'-, \ -R'-CO-, \ -R'-NHCO-, \ -R'-NHCONH-R''-NHCO-, \ -R'-OCONH-R''-NHCO-$$

where R' is a divalent alkylene group, such as ethylene, propylene or butylene, and R'' is identical to R' or to an arylene group such as:

$$-C_6H_4-, \ -C_6H_4-C_6-H_4-, \ -C_6H_4-CH_2-C_6H_4-, \ -C_6H_4-CH(CH_3)_2-C_6H_4-$$

and preferably phenylene.

The preferential organic divalent groups are selected from among:

$$-CH_2-CH_2-, \ -C_3H_6-, \ -C_4H_8-, \ -(CH_2)_2-CO-, \ -(CH_2)_3-NHCO-, \ -(CH_2)_3-NHCONHC_6H_4NHCO- \text{ and } -(CH_2)_3-OCONHC_6H_4NHCO-$$

The copolymers conforming to the present invention are known and described in Application No. EP-0 492 657.

The polydimethylsiloxane/polyoxyalkylene block copolymers, particularly preferred according to the invention, are selected from among those with the following formula (IA):

$$[C_4H_8O(C_nH_{2n}O)_bC_4H_8SiMe_2O(SiMe_2O)_aSiMe_2]_c \qquad (IA)$$

where Me is methyl, n is an integer from 2 to 4, a and b are integers of at least 4, and c is a number of at least 4.

Among these copolymers, use is more particularly made of those having a recurrent motif with the formula:

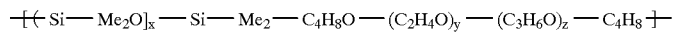

where x is a number between 5 and 15 inclusive, y is a number between 15 and 30 inclusive, and z is a number between 20 and 40 inclusive.

The polydimethylsiloxane/polyoxyalkylene block copolymers are present in the compositions in proportions of between 0.1 and 5% by weight, and preferably between 0.5 and 3% by weight of the total weight of the composition.

The alkylpolyglycosides usable according to the invention answer in particular to the following formula (II):

$$R(C_6H_{10}O_5)_x\text{—H} \tag{II}$$

where R is defined by:

$$R_1\text{—O—}(R_2O)_m\text{—}$$

where $R_1$ is a branched or linear alkyl group, having 8 to 18 carbon atoms, a branched or linear alkenyl group having 8 to 18 carbon atoms, or an alkylphenyl group having 8 to 18 carbon atoms, and where the alkyl portion is either linear or branched, and $R_2$ is an alkylene group having 2 to 4 carbon atoms, and where m is between 0 and 10.

The preferred compounds are those in which $R_1$ is an alkyl group having 8 to 18 carbon atoms, and preferably 10 to 14 carbon atoms, such as the decyl, lauryl and myristyl groups.

The preferable value of m is between 0 and 3, and the most preferable value is 0. x is a number between 1 and 10.

The alkylpolyglycoside compounds with the developed formula (IV) defined below, used according to the invention, are preferably represented by the products sold by the company Henkel under the denomination APG, such as the products APG 300, APG 350, APG 500, APG 550, APG 625, APG base 10–12, and Plantaren 1300, 1200 UP and 2000 UP, by the products sold by the company SEPPIC under the denominations Triton CG 110 (or Oramix CG 110) and Triton CG 312 (or Oramix NS 10), and those sold by the company BASF under the denomination Lutensol GD 70.

The non-ionic surfactants of the polyglycerol type used according to the present invention are selected preferably from among the following polyhydroxypropylether compounds:

(A) Compounds answering to the formula (IV):

$$RO[(C_3H_5(OH)\text{—})]_n\text{H} \tag{IV}$$

in which the [$C_3H_5$(OH)] group represents the following structures, used together or separately:

$$\text{—}(CH_2CHOH\text{—}CH_2\text{—}O)\text{—} \tag{IVa}$$

$$\text{—}(CH_2\text{—}CH\text{—}O)\text{—} \quad \text{and} \tag{IVb}$$
$$\quad\quad |$$
$$\quad CH_2OH$$

$$\text{—}(CH\text{—}CH_2\text{—}O)\text{—} \tag{IVc}$$
$$\quad |$$
$$CH_2OH$$

and R and n have the following meanings:
(a) R is a radical or a mixture of $C_{10}$–$C_{14}$ alkyl radicals and n is a whole or decimal number from 2 to 10 and preferably from 3 to 6.
(b) R is a remnant:

$$R_2\text{ CONH }CH_2\text{—}CH_2O\text{ }CH_2\text{—}CH_2 \tag{V}$$

where $R_2$ denotes a radical or a mixture of alkyl and/or alkenyl radicals in $C_{11}$–$C_{17}$ and n denotes a whole or decimal number from 1 to 5 and preferably from 1.5 to 4.

(c) R is a remnant:

$$R_3\text{—CHOH—}CH_2 \tag{VI}$$

where $R_3$ denotes an aliphatic, cycloaliphatic, arylaliphatic radical in $C_7$–$C_{21}$ and their mixtures, the aliphatic chains denoting in particular the alkyl chains having 1 to 6 ether, thioether and/or hydroxymethylene groups, and n denotes a whole or decimal number from 1 to 10.

These surfactants with the formula (IV) can be prepared by the processes described in French Patents Nos. 1.477.048, 2.328.763 and 2.091.516.

(B) The compounds prepared by condensation, in acidic catalysis, of 2 to 10 and preferably of 2.5 to 6 moles of glycidol per mole of alcohol or alpha-diol containing 10 to 14 carbon atoms, at a temperature from 50 to 120° C., the glycidol being added slowly to the alcohol or to the alpha-diol. The process of preparation of these compounds is described in French Patent No. A-2.169.787.

(C) The polyhydroxypropylether compounds prepared by polyaddition of glycerol monochlorhydrin to a polyhydroxyl organic compound in the presence of a strong base, with progressive removal of water by distillation. These compounds are described in French Patent No. A2.574.786.

Among the non-ionic surfactants of the polyhydroxypropylether family described in sections (A), (B) and (C) above, the preferred compounds are represented by the formulas:

$$(\alpha)\quad C_{12}H_{25}O\text{—}(CH_2\text{—}CH\text{—}O)_{\overline{4,2}}H \tag{VII}$$
$$\quad\quad\quad\quad\quad\quad\quad\quad\quad |$$
$$\quad\quad\quad\quad\quad\quad\quad CH_2OH$$

$$R_1O\text{—}(CH_2\text{—}CH\text{—}O)_{\overline{3,75}}H \tag{VIII}$$
$$\quad\quad\quad\quad\quad |$$
$$\quad\quad\quad CH_2OH$$

where R1 denotes a mixture of alkyl radicals in C10H21 and C12H25.

(β) The compounds prepared by condensation in alkaline catalysis, of 3.5 moles of glycidol on an alpha-diol having 12 carbon atoms, according to the process described in French Patent No. A-2.091.516.

(γ) The compounds answering to the formula:

$$R_2\text{—CONH—}CH_2\text{—}CH_2\text{—O—}CH_2\text{—}CH_2\text{—O—}(CH_2\text{—CHOH-}$$
$$CH_2O)_{3,5}\text{—H} \tag{IX}$$

where R2 denotes a mixture of radicals containing the following alkyl and alkenyl radicals: $C_{11}H_{23}H_{27}$, the radicals derived from fatty acids of copra and the radical derived from oleic acid.

(δ) The compounds prepared by condensation of 3.5 moles of glycidol on a mixture of alpha-diols in $C_{11}C_{14}$, described in French Patent No. A-2.091.516.

The non-ionic surfactant polyhydroxypropylether obtained by condensation of glycerol monochlorhydrin (2.5 moles) in the presence of caustic soda on dodecanediol-1,2 is more particularly preferred.

If the compositions according to the invention are not used for the washing of keratinic materials, the non-ionic surfactant or surfactants of the alkylpolyglycoside and/or polyglycerol type are used in such compositions in proportions preferably of between 0.05 and 5% by weight of the total weight of the composition. These compositions are used in particular as rinsing compositions, applied before or after shampoo, dyeing, bleaching, permanent wave, straightening, as a dyeing or permanent wave composition, or as a non-rinsed hair styling, care or protection composition.

If the compositions according to the invention are washing compositions, they contain the non-ionic surfactant or surfactants of the alkylpolyglycoside and/or polyglycerol type in proportions of between 1 and 30% by weight of the total weight of the composition and more particularly between 5 and 20% by weight.

The pH of the compositions according to the invention is generally between 2 and 10, and more particularly between 4 and 8.

In so far as the cosmetically acceptable medium of the composition according to the invention is an aqueous medium, it may consist exclusively of water or of a mixture of water and a cosmetically acceptable solvent, such as the lower $C_1$–$C_4$ alcohols, like ethanol, isopropanol, and n-butanol, and alkylene glycols, such as propylene glycol, and glycol ethers.

The compositions according to the invention can be presented in the form of liquids of varying consistency, gels, emulsions (milks or creams), aqueous or hydro-alcoholic lotions, dispersions, or aerosol foams.

The compositions are, for example, emollient lotions, milks or creams, milks or creams for the care of keratinic materials, cleansing creams or milks, bases of make-up foundations, sun-protection lotions, milks or creams, artificial tanning lotions, milks or creams, shaving creams or foams, after-shave lotions, face packs, make-up products for the eyes, eyelashes or eyebrows, make-up and make-up foundations for the face, nail varnish, shampoo, bath and shower products, compositions to be rinsed or not, to be applied before or after shampoo, dyeing, bleaching, permanent wave or straightening, as a dyeing composition.

The compositions according to the invention may also contain, in addition, various additives, which do not deteriorate the properties of the composition, such as anionic, cationic, amphoteric or zwitterionic surfactants, non-ionic surfactants other than those described previously, acidizing or alkalinizing agents, preservatives, thickeners, suspending agents, softeners, sun filters, perfumes, biocides, antioxidants, pigments, dyes, pearl lustering agents, biocides, repellants, oxidants, reducing agents, moisturizers, vitamins, preservatives, foam reinforcers, electrolytes, cerarnides, UV filters, anti-bacterial agents, anti-dandruff agents, anti-seborrhoeic agents, pesticides, or other additives routinely used in cosmetics.

The compositions according to the invention are applied to the skin or hair in a cosmetically effective quantity, depending on the type of composition concerned.

One particular application of the compositions according to the invention is the application as a washing and cosmetic treatment composition for keratinic materials, preferably for the skin and hair, and more particularly as a shampoo. In this particular case, the shampoo is applied to the wet or dry hair in effective quantities to wash it, this application being followed by rinsing.

The following examples are intended to illustrate the invention but without being in any way limitative.

EXAMPLE 1

A shampoo with the following composition is prepared:

| | |
|---|---|
| Alkyl(C8–C10) polyglycoside sold in aqueous solution containing 60% AM under the denomination 'Oramix CG 110' by the company SEPPIC | 18 g AM |
| Block copolymer with the formula: $[[(CH_3)_2SiO]x(CH_3)_2SiCH_2CH(CH_3)CH_2O(C_2H_4O)_y\text{—}(C_3H_6O)zCH_2CH(CH_3)CH_2]_n$ where x = 9 to 11, y = 18 to 25, z = 28 to 35, and n in ethanol solution containing 70% AM, and such that the viscosity of a 10% solution of polymer in ethanol is about 50 mPa s | 3 g AM |
| Heptamethylnonane sold under the denomination 'Arlamol HD' by the company ICI | 3 g |
| Derivative of polyethylene glycol dioleate (55 moles of ethylene oxide) and of propylene glycol, sold under the denomination 'Antil 141 Liquide' by the company Goldschmidt containing 43.6% AM | 2 g AM |
| Perfume, preservative qs | |
| Sodium hydroxide qs, pH = 5.5 | |
| Water qsp | 100 g |

EXAMPLE 2

A shampoo with the following composition is prepared:

| | |
|---|---|
| Alkyl($C_9$—$C_{10}$—$C_{11}$/20-4040) polyglycoside (1,4), sold containing 50% AM under the denomination 'APG 300' by the company Henkel | 15 g AM |
| Polyether urethane sold under the denomination 'Dapral T212' by the company Akzo | 3 g |
| $[[(CH_3)_2SiO]x(CH_3)_2SiCH_2CH(CH_3)CH_2O(C_2H_4O)_y\text{—}(C_3H_6O)zCH_2CH(CH_3)CH_2]_n$ with x = 9 to 11, y = 18 to 25, z = 28 to 35, and n in ethanol solution containing 70% AM, and such that the viscosity of a 10% solution of polymer in ethanol is about 50 mPa s | 2.5 g AM |
| Polymer of hydroxyethylcellulose and epichlorhydrin quaternized with trimethylamine, sold under the denomination 'Celquat SC 240' by the company National Starch | 1 g |
| Perfume, preservative qs | |
| Sodium hydroxide qs, pH = 6.5 | |
| Water qsp | 100 g |

EXAMPLE 3

An after-shampoo for rinsing with the following composition is prepared:

| | |
|---|---|
| Alkyl(C9-C10-C11/20-4040) polyglycoside (1,4), sold containing 50% AM under the denomination 'APG 300' by the company Henkel | 1 g AM |
| $[[(CH_3)_2SiO]x(CH_3)_2SiCH_2CH(CH_3)CH_2O(C_2H_4O)_y\text{—}(C_3H_6O)zCH_2CH(CH_3)CH_2]_n$ with x = 9 to 11, y = 18 to 25, z = 28 to 35, and n in ethanol solution containing 70% AM, and such that the viscosity of a 10% solution of polymer in ethanol is about 50 mPa s | 2.5 g AM |
| Polyacrylamide emulsion sold under the denomination 'Sepigel 305' by the company SEPPIC | 0.25 g of polymer |
| Perfume, preservative qs | |
| Spont pH = 4.3 | |
| Water qsp | 100 g |

We claim:

1. A cosmetic composition consisting essentially of, in a cosmetically acceptable aqueous medium, 0.05 to 30% by weight of the total weight of the composition of at least one non-ionic surfactant selected from the group consisting of an alkylpolyglycoside surfactant and a polyglycerol surfactant, and 0.1 to 5% by weight of the total weight of the composition of at least one polydimethylsiloxane/polyoxyalkylene block copolymer, said polydimethylsiloxane/polyoxyalkylene block copolymer has the following formula $$([Y((R_2)SiO)_a(R_2)SiYO][(C_nH_{2n}O)_b])_c \quad (I)$$

where

R identical or different, denotes a methyl, ethyl, propyl, butyl, pentyl or hexyl, n is 2, 3 or 4, a is an integer not less than 5, b is an integer not less than 4, c is a number not less than 4, Y denotes a group selected from among:

$$-R'-, -R'-CO-, \text{ and } -R^1-NHCO-,$$

where

R' of Y in formula (I) is selected from the group consisting of ethylene, propylene and butylene, said alkylpolyglycoside surfactant has the following formula (II):

$$R(C_6H_{10}O_5)_x-H \quad (II)$$

where

R (of formula II) is defined by:

$$R_1-O-$$

where $R_1$ is a branched or linear alkyl group having 8 to 18 carbon atoms, a branched or linear alkenyl group having 8 to 18 carbon atoms, or an alkylphenyl group having 8 to 18 carbon atoms, the alkyl portion of said alkylphenyl group being either linear or branched, and where x denotes a number between 1 and 10; and said polyglycerol surfactant is selected from among the following polyhydroxypropylethers:

compounds of the formula (IV):

$$RO[C_3H_5(OH)-O-]_n-H \quad (IV)$$

in which the $[C_3H_5(OH)-O-]$ group represents at least one of the following structures:

$$-\!\!\!+\!CH_2CHOH-CH_2-O-\!\!\!+\!\!- \quad (IVa)$$

$$-\!\!\!+\!CH_2-CH-O-\!\!\!+\!\!- \quad \text{and} \quad (IVb)$$
$$\qquad\quad |$$
$$\qquad\quad CH_2OH$$

$$-\!\!\!+\!CH-CH_2-O-\!\!\!+\!\!- \quad (IVc)$$
$$\quad |$$
$$\quad CH_2OH$$

and R and n (of formula IV) have the following meanings:

(a) R is a radical or a mixture of $C_{10}$–$C_{14}$ alkyl radicals and n is a whole or decimal number from 2 to 10;

(b) R is $$R_2CONHCH_2-CH_2OCH_2-CH_2- \quad (V)$$

where $R_2$ denotes a radical or a mixture of alkyl or alkenyl radicals of $C_{11}$–$C_{17}$ and n denotes a whole or decimal number from 1 to 5; or (c) R is $$R_3-CHOH-CH_2- \quad (VI)$$

where $R_3$ denotes an aliphatic, cycloaliphatic, arylaliphatic radical of $C_7$–$C_{21}$ and their mixtures, and n denotes a whole or decimal number from 1 to 10.

2. The composition of claim 1, wherein the polydimethylsiloxane/polyoxyalkylene block copolymer of formula (I) has an average molecular weight greater than or equal to 3000; the average molecular weight of each polyalkylene or siloxane block being between 300 and 10,000 and the proportion of siloxane blocks being between 10 and 95% by weight of the total weight of the block copolymer.

3. The composition of claim 1 where the polydimethylsiloxane/polyoxyalkylene block copolymer corresponds to the following formula (IA):

$$[C_4H_8O(C_nH_{2n}O)_bC_4H_8SiMe_2O(SiMe_2O)_aSiMe_2]_c \quad (IA)$$

where a is an integer greater than or equal to 4, b is an integer greater than or equal to 4, c is a number greater than or equal to 4, and n is an integer from 2 to 4.

4. The composition of claim 1 wherein the polydimethylsiloxane/polyoxyalkylene block copolymer has a recurrent motif with the following structure:

$$-\!\!\![-(Si-Me_2O)_x-Si-Me_2-C_4H_8O-(C_2H_4O)_y-(C_3H_6O)_z-$$
$$C_4H_8-]\!\!-$$

in which x is between 5 and 15 inclusive, y is between 15 and 30 inclusive, and z is between 20 and 30 inclusive.

5. The composition according to claim 1 where said polyhydroxypropylethers are compounds of formula (IV), n is a whole number or decimal number from 3 to 6.

6. The composition according to claim 1 where when R of said polyhydroxypropylethers is a compound of formula (V), n is a whole or decimal number from 1.5 to 4.

7. The composition according to claim 1 where when R of said polyhydroxypropylethers is a compound of formula (VI), said aliphatic, cycloaliphatic or arylaliphatic radicals further contain 1–6 ether, thioether or hydroxymethylene groups.

8. The composition of claim 1, wherein the polyglycerolated non-ionic surfactants are selected from among the following polyhydroxypropylethers:

$$(\alpha) \quad C_{12}H_{25}O-(CH_2-CH-O-)_{\overline{4.2}}H \quad (VII)$$
$$\qquad\qquad\qquad\qquad\qquad |$$
$$\qquad\qquad\qquad\qquad\qquad CH_2OH$$

-continued $$R_1O-(CH_2-CH-O)_{3.75}H \quad | \quad CH_2OH \tag{VIII}$$

where
$R_1$ denotes a mixture of alkyl radicals $C_{10}H_{21}$ and $C_{12}H_{25}$;

(β) compounds prepared by condensation, in alkaline catalysis, of 3.5 moles of glycidol on an alpha-diol having 12 carbon atoms;

(γ) compounds of the formula:

$$R_2-CONH-CH_2-CH_2-O-CH_2-CH_2-O-(CH_2-CHOH-CH_2-O-)_{3.5}-H \tag{IX}$$

where
$R_2$ denotes a mixture of radicals containing the following alkyl and alkenyl radicals: $C_{11}H_{23}H_{27}$, the radicals derived from fatty acids of copra and the radical derived from oleic acid; and (δ) compounds prepared by condensation of 3.5 moles of glycidol on a mixture of alpha-diols in $C_{11}$–$C_{14}$.

9. The composition of claim 1 wherein said composition contains 0.05 to 5% by weight of the total weight of said composition of said non-ionic surfactant.

10. The composition of claim 1 wherein the cosmetically acceptable aqueous medium consists exclusively of water or of a mixture of water and a cosmetically acceptable solvent.

11. The composition of claim 1 further comprising anionic, cationic, amphoteric or zwitterionic surfactants, non-ionic surfactants other than those described previously, acidizing or alkalinizing agents, preservatives, thickeners, suspending agents, softeners, sun filters, perfumes, biocides, anti-oxidants, pigments, dyes, pearl lustering agents, repellents, oxidants, reducing agents, moisturizers, vitamins, foam reinforcers, electrolytes, ceramides, UV filters, anti-bacterial agents, anti-dandruff agents, anti-seborrhoeic agents, or pesticides.

12. The composition of claim 1 wherein said composition contains 1 to 30% by weight of the total weight of said composition of said non-ionic surfactant.

13. A cosmetic composition consisting essentially of, in a cosmetically acceptable aqueous medium, 0.05 to 30% by weight of the composition of at least one polyglycerol surfactant, and 0.1 to 5% by weight of the composition of at least one polydimethylsiloxane/polyoxyalkylene block copolymer, said polydimethylsiloxane/polyoxyalkylene block copolymer has the following formula $$([Y((R_2)SiO)_a(R_2)SiYO][(C_nH_{2n}O)_b])_c \tag{I}$$

where
R identical or different, denotes a methyl, ethyl, propyl, isopropyl, butyl, pentyl or hexyl,
n is 2, 3 or 4,
a is an integer not less than 5,
b is an integer not less than 4,
c is a number not less than 4,
Y denotes a group selected from among:

—R'—, —R'—CO—, and —R'—NHCO—, where
R' of Y in formula (I) is selected from the group consisting of ethylene, propylene and butylene, said polyglycerol surfactant is selected from among the following polyhydroxypropylethers:
compounds of the formula (IV):

$$RO[C_3H_5(OH)-O-]_n-H \tag{IV}$$

in which the $[C_3H_5(OH)-O-]$ group represents at least one of the following structures:

$$+CH_2CHOH-CH_2-O+ \tag{IVa}$$

$$+CH_2-CH-O+ \quad | \quad CH_2OH \tag{IVb}$$

and $$+CH-CH_2-O+ \quad | \quad CH_2OH \tag{IVc}$$

and R and n (of formula IV) have the following meanings:
(a) R is a radical or a mixture of $C_{10}$–$C_{14}$ alkyl radicals and n is a whole or decimal number from 2 to 10;
(b) R is $$R_2CONHCH_2-CH_2OCH_2-CH_2- \tag{V}$$

where
$R_2$ denotes a radical or a mixture of alkyl or alkenyl radicals of $C_{11}$–$C_{17}$ and
n denotes a whole or decimal number from 1 to 5; or
(c) R is $$R_3-CHOH-CH_2- \tag{VI}$$

where
$R_3$ denotes an aliphatic, cycloaliphatic, arylaliphatic radical of $C_7$–$C_{21}$ and their mixtures, and
n denotes a whole or decimal number from 1 to 10.

14. The composition of claim 13, wherein the polydimethylsiloxane/polyoxyalkylene block copolymer of formula (I) has an average molecular weight greater than or equal to 3000; the average molecular weight of each polyalkylene or siloxane block being between 300 and 10,000 and the proportion of siloxane blocks being between 10 and 95% by weight of the total weight of the block copolymer.

15. The composition of claim 13 where the polydimethylsiloxane/polyoxyalkylene block copolymer corresponds to the following formula (IA):

$$[C_4H_8O(C_nH_{2n}O)_bC_4H_8SiMe_2O(SiMe_2O)_aSiMe_2]_c \tag{IA}$$

where
a is an integer greater than or equal to 4,
b is an integer greater than or equal to 4,
c is a number greater than or equal to 4, and
n is an integer from 2 to 4.

16. The composition of claim 13 wherein the polydimethylsiloxane/polyoxyalkylene block copolymer has a recurrent motif with the following structure:

$$+[-(Si-Me_2O)_x-Si-Me_2-C_4H_8O-(C_2H_4O)_y-(C_3H_6O)_z-C_4H_8-]+$$

in which
x is between 5 and 15 inclusive, y is between 15 and 30 inclusive, and z is between 20 and 30 inclusive.

17. The composition according to claim 13 where said polyhydroxypropylethers are compounds of formula (IV), n is a whole number or decimal number from 3 to 6.

18. The composition according to claim 13 where when R of said polyhydroxypropylethers is a compound of formula (V), n is a whole or decimal number from 1.5 to 4.

19. The composition according to claim 13 where when R of said polyhydroxypropylethers is a compound of formula (VI), said aliphatic, cycloaliphatic or arylaliphatic radicals further contain 1–6 ether, thioether or hydroxymethylene groups.

20. The composition of claim 13, wherein the polyglycerolated non-ionic surfactants are selected from among the following polyhydroxypropylethers:

(α) $C_{12}H_{25}O-(CH_2-\underset{\underset{CH_2OH}{|}}{CH}-O)_{\overline{4,2}}H$ (VII)

$R_1O-(CH_2-\underset{\underset{CH_2OH}{|}}{CH}-O)_{\overline{3,75}}H$ (VIII)

where $R_1$ denotes a mixture of alkyl radicals of $C_{10}H_{21}$ and $C_{12}H_{25}$;

(β) compounds prepared by condensation, in alkaline catalysis, of 3.5 moles of glycidol on an alpha-diol having 12 carbon atoms;

(γ) compounds of the formula:

$R_2-CONH-CH_2-CH_2-O-CH_2-CH_2-O-(CH_2-CHOH-CH_2-O-)_{3.5}-H$ (IX)

where $R_2$ denotes a mixture of radicals containing the following alkyl and alkenyl radicals: $C_{11}H_{23}H_{27}$, the radicals derived from fatty acids of copra and the radical derived from oleic acid; and (δ) compounds prepared by condensation of 3.5 moles of glycidol on a mixture of alpha-diols in $C_{11}-C_{14}$.

21. The composition of claim 13 wherein said composition contains 0.05 to 5% by weight of the total weight of said composition of said polyglycerol surfactant.

22. The composition of claim 13 wherein the cosmetically acceptable aqueous medium consists exclusively of water or of a mixture of water and a cosmetically acceptable solvent.

23. The composition of claim 13 further comprising anionic, cationic, amphoteric or zwitterionic surfactants, non-ionic surfactants other than those described previously, acidizing or alkalinizing agents, preservatives, thickeners, suspending agents, softeners, sun filters, perfumes, biocides, anti-oxidants, pigments, dyes, pearl lustering agents, repellents, oxidants, reducing agents, moisturizers, vitamins, foam reinforcers, electrolytes, ceramides, UV filters, anti-bacterial agents, anti-dandruff agents, anti-seborrhoeic agents, or pesticides.

24. The composition of claim 13 wherein said composition contains 1 to 30% by weight of the total weight of said composition of said polyglycerol surfactant.

* * * * *